United States Patent [19]

Herrmann et al.

[11] Patent Number: 4,482,764

[45] Date of Patent: Nov. 13, 1984

[54] PREPARATION OF DIOLS

[75] Inventors: Guenter Herrmann, Neustadt; Elmar Frommer, Ludwigshafen; Juergen Paetsch, Wachenheim; Wolfgang Reiss, Ludwigshafen; Siegfried Winderl, Heidelberg-Wieblingen, all of Fed. Rep. of Germany

[73] Assignee: BASF Aktiengesellschaft, Fed. Rep. of Germany

[21] Appl. No.: 203,448

[22] Filed: Nov. 3, 1980

[51] Int. Cl.$^3$ .................... C07C 29/136; C07C 31/16
[52] U.S. Cl. ...................................... 568/864; 568/885
[58] Field of Search ........................................ 568/864

[56] References Cited

U.S. PATENT DOCUMENTS

| | | | |
|---|---|---|---|
| 2,044,417 | 6/1936 | Balcar | 568/898 |
| 3,478,112 | 11/1969 | Adam et al. | 568/864 |
| 3,752,861 | 8/1973 | Hobbs et al. | 568/864 |
| 3,862,249 | 1/1975 | Ester et al. | 568/896 |
| 3,898,290 | 8/1975 | Ester | 568/896 |
| 4,150,245 | 4/1979 | Sommer et al. | 568/896 |

FOREIGN PATENT DOCUMENTS

| | | |
|---|---|---|
| 1046610 | 12/1958 | Fed. Rep. of Germany . |
| 2124126 | 11/1972 | Fed. Rep. of Germany . |
| 2819593 | 11/1979 | Fed. Rep. of Germany ...... 568/864 |

*Primary Examiner*—J. E. Evans
*Attorney, Agent, or Firm*—Keil & Weinkauf

[57] ABSTRACT

The hydrogenation of carboxylic acids having 6 or less C atoms, as obtained as by-products of cyclohexane oxidation, to give corresponding diols is improved by the addition of a small amount of phosphoric acid or a phosphoric ester before hydrogenation.

6 Claims, No Drawings

PREPARATION OF DIOLS

One of the methods of preparing, for example, hexane-1,6-diol, is the catalytic hydrogenation of mixtures containing adipic acid and other $C_6$-carboxylic acids which are obtained together with other, shorter-chain carboxylic acids, as a by-product of the oxidation of cyclohexane.

The literature concerned with the oxidation of cyclohexane, for example German Pat. No. 1,046,610, in most cases only makes passing mention of the formation of this carboxylic acid mixture.

Since the oxidation of cyclohexane (which is ultimately used to produce, via cyclohexanone and its oxime, $\Sigma$-caprolactam, the raw material for nylon-6) is a large-scale industrial process, the working up of the by-product streams is also industrially important.

The hydrogenation of the carboxylic acid mixture suffers from a problem which, though it has no major quantitative effect on the outcome of the reaction, does cause blockages of the equipment. This is referred to as cork formation; the residues deposited cannot be defined more closely. Nor have the composition of the mixtures to be hydrogenated or the composition of their impurities given any closer indication as to how this problem can be overcome.

A typical carboxylic acid mixture to be hydrogenated has, for example, the following composition:

| | |
|---|---|
| Water | about 65% |
| Adipic acid | 15% |
| Hydroxycaproic acid | 12% |
| Glutaric acid | 2% |
| Succinic acid | 0.7% |
| Formic acid and higher fatty acids | 2% |

We have found that the problem can be overcome by addition of a small amount of phosphoric acid or of a phosphoric acid derivative. In general, from 10 to 100 ppm, based on the aqueous solutions, suffices. Depending on the severity of the problem observed, the addition of, for example, from 1 to 1,000 ppm may be advisable.

In addition to phosphoric acid itself, esters of phosphoric acid, for example with alcohols of 1 to 20 carbon atoms, may be used. Examples of suitable esters are acid and neutral, individual or mixed, esters of phosphoric acid with butanol, 2-ethylhexanol and isotridecanol.

An outwardly similar measure is to be found only in German Laid-Open Application DOS No. 2,124,124, where phosphoric acid esters are added during the decomposition of peroxides formed on oxidation of cyclohexane. This process is however in no way related to the present invention; rather, the similarity is purely accidental. Furthermore, in the known process, only the esters, but not the free acids, are effective.

EXAMPLE

Mixtures having the composition shown above are hydrogenated, over a cobalt catalyst, in an installation comprising a supply tank, heat exchangers, a reactor of 10 $m^3$ useful capacity and conventional accessories. The reactor and heat exchangers require cleaning at intervals of about 2 weeks.

After addition of 50 ppm of phosphoric acid tridecanolate (a mixture of the monoester and the diester) to the contents of the supply tank, more than a year can be allowed to elapse between cleanings. If, in place of using the phosphoric acid ester, a concentration of 50 ppm of phosphoric acid is maintained in the supply tank, cleaning intervals of a year or more are, once again, feasible. The criteria used to indicate that cleaning is necessary are the heat transfer in the heat exchanger (steam consumption) and the pressure rise in the reactor.

We claim:

1. A process for preparing $\alpha,\omega$-diols of not more than 6 carbon atoms by hydrogenating in a reactor a mixture of corresponding monocarboxylic and dicarboxylic acids, as obtained as by-products of the oxidation of cyclohexane to cyclohexanone, wherein an effective amount sufficient to prevent deposit of residues in the reactor or in heat exchangers associated with the reactor of phosphoric acid itself or of a phosphoric acid ester, said effective amount being within the range of from 1 to 1000 ppm, is added to the monocarboxylic and dicarboxylic acids or their mixtures before the hydrogenation.

2. A process as claimed in claim 1, wherein said phosphoric ester is an ester of phosphoric acid and an alcohol of 1 to 20 carbon atoms.

3. A process as claimed in claim 1, wherein said phosphoric ester is an ester of phosphoric acid and butanol, 2-ethylhexanol or isotridecanol.

4. A process as claimed in claim 1, wherein said mixture of acids embodies adipic acid, hydroxycaproic acid, glutaric acid, succinic acid, formic acid and higher fatty acids.

5. A process as claimed in claim 1, wherein said ester is a mixture of phosphoric acid tridecanolate monester and diester.

6. A process as claimed in claim 1, wherein the hydrogenation of said mixtures of monocarboxylic and dicarboxylic acids is carried out in the presence of a cobalt catalyst.

* * * * *